US011332708B2

(12) United States Patent
Baek et al.

(10) Patent No.: US 11,332,708 B2
(45) Date of Patent: May 17, 2022

(54) **MICROORGANISM OF THE GENUS *CORYNEBACTERIUM* PRODUCING 5'-XANTHOSINE MONOPHOSPHATE AND METHOD FOR PREPARING 5'-XANTHOSINE MONOPHOSPHATE USING THE SAME**

(71) Applicant: CJ CHEILJEDANG CORPORATION, Seoul (KR)

(72) Inventors: Min Ji Baek, Gyeonggi-do (KR); Ji Hye Lee, Gyeonggi-do (KR); Boram Lim, Gyeonggi-do (KR); Byoung Hoon Yoon, Seoul (KR); Jeong Eun Lee, Daegu (KR); Su-bin Lim, Gyeonggi-do (KR); Jaeho Jeong, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 90 days.

(21) Appl. No.: 17/076,074

(22) Filed: Oct. 21, 2020

(65) Prior Publication Data

US 2021/0040441 A1 Feb. 11, 2021

Related U.S. Application Data

(63) Continuation of application No. 16/465,774, filed as application No. PCT/KR2018/007027 on Jun. 21, 2018, now Pat. No. 10,844,348.

(30) Foreign Application Priority Data

Jun. 7, 2018 (KR) .......................... 10-2018-0065681

(51) Int. Cl.
| | | |
|---|---|---|
| C12N 1/20 | (2006.01) | |
| C12N 15/17 | (2006.01) | |
| C12N 15/67 | (2006.01) | |
| C12N 15/77 | (2006.01) | |
| C12P 19/40 | (2006.01) | |

(52) U.S. Cl.
CPC .............. *C12N 1/20* (2013.01); *C12N 15/67* (2013.01); *C12N 15/77* (2013.01); *C12P 19/40* (2013.01)

(58) Field of Classification Search
CPC ............ C12N 1/20; C12N 15/17; C12P 19/40
See application file for complete search history.

(56) References Cited

U.S. PATENT DOCUMENTS 6,822,084 B1 * 11/2004 Pompejus ................ C12P 13/12
536/23.7
2014/0080185 A1   3/2014 Takeshita et al.

FOREIGN PATENT DOCUMENTS

| KR | 10-0620092 B1 | 9/2006 |
| KR | 10-2009-0080654 A | 7/2009 |
| KR | 10-2010-0070219 A | 6/2010 |
| KR | 10-2011-0105662 A | 9/2011 |

OTHER PUBLICATIONS

Dr. Jyoti (Controller), Office Action dated Aug. 31, 2021 for corresponding Indian Patent Application No. 201917025956, 7 pages.
Altschul et al., "Gapped BLAST and PSI-BLAST: a new generation of protein database search programs", Nucleic Acids Research, 1997, vol. 25, No. 17, pp. 3389-3402.
Shinichi et al., "Dynamical aspects of protein structures revealed by newly established NMR approach", Journal of Japanese Biochemical Society, 2013, vol. 85, No. 8, pp. 638-645, with English translation of p. 638.
Hayashi et al., "Research on the Development of Innovative Application and Modifying Technology for the Carbohydrate Relating Enzymes", Bulletin of Applied Glycoscience, 2012, vol. 2, No. 1, pp. 33-43, with English translation of pp. 33-34.
Kenji et al., "Functional modification of arylmalonic acid decarboxylase", The Society for Bioscience and Bioengineering, 2014, vol. 92, No. 8, pp. 424-427, with English translation of p. 424.
GenBank Accession No. WP_088859234, MFS transporter [Corynebacterium stationis], Jul. 7, 2017, 1 Page.
Noguchi et al., "31P NMR studies of energy metabolism in xanthosine-5'-monophosphate overproducing Corynebacterium ammoniagenes", Eur. J. Biochem., 2003, vol. 270, pp. 2622-2626.
van der Rest et al., "A heat shock following electroporation induces highly efficient transformation of Corynebacterium glutamicum with xenogeneic plasmid DNA", Appl Microbiol Biotechnol, 1999, vol. 52, pp. 541-545.
Communication pursuant to Article 94(3) EPC dated Sep. 10, 2020 for corresponding European Application No. 18899009.7, 4 pages.
Corynebacterium stationis strain LMG 21670, complete genome, Accession No. CP019963, cited in Lee et al., "The whole genome sequencing and assembly of Corynebacterium stationis LMG 2160T strain", Mar. 11, 2017, retrieved inline from EBI accession No. EM_STD:CP019963 Database accession No. CPO19963.
Corynebacterium stationis strain ATCC 21170, genome, Accession No. CP016326, cited in Yang et al., Genome sequence of Corynebacterium stationis ATCC 21170, Jul. 7, 2017, retrieved online from EBI accession No. EM_STD: CP016326 Database accession No. CP016326.

* cited by examiner

*Primary Examiner* — Tekchand Saidha
(74) *Attorney, Agent, or Firm* — MH2 Technology Law Group, LLP

(57) ABSTRACT

The present disclosure relates to a microorganism of the genus *Corynebacterium* producing 5'-xanthosine monophosphate and a method for producing 5'-xanthosine monophosphate using the same.

4 Claims, No Drawings
Specification includes a Sequence Listing.

MICROORGANISM OF THE GENUS *CORYNEBACTERIUM* PRODUCING 5'-XANTHOSINE MONOPHOSPHATE AND METHOD FOR PREPARING 5'-XANTHOSINE MONOPHOSPHATE USING THE SAME

CROSS-REFERENCE TO RELATED APPLICATIONS

This application is a continuation of U.S. patent application Ser. No. 16/465,774 filed 31 May 2019, which is a U.S. National Stage application of PCT/KR2018/007027 filed 21 Jun. 2018, which claims priority to Korean Patent Application No. 10-2018-0065681 filed 7 Jun. 2018, the entire disclosures of which are herein incorporated by reference.

SEQUENCE LISTING

The instant application contains a Sequence Listing which has been submitted electronically in ASCII format and is hereby incorporated by reference in its entirety. Said ASCII copy, created on 23 May 2019, is named 0312_0004-US_SL.txt and is 11 Kilobytes in size.

TECHNICAL FIELD

The present disclosure relates to a microorganism producing 5'-xanthosine monophosphate and a method for producing 5'-xanthosine monophosphate using the same.

BACKGROUND ART

5'-Xanthosine monophosphate (XMP) not only has physiological significance in animals and plants as an intermediate in nucleic acid biosynthesis and metabolic systems, but is also used for various purposes: foods, medicine, and various medical uses. In particular, when used together with monosodium glutamate (MSG), there is a synergistic effect in enhancing flavors. Accordingly, XMP is one of the nucleic acid-based flavor enhancers that have drawn attention as a seasoning.

Further, 5'-xanthosine monophosphate is an intermediate in purine nucleotide biosynthesis metabolism, and is an important raw material for the production of 5'-guanosine monophosphate (GMP). A well-known method for preparing guanosine monophosphate that has high commercial value and affects in increasing the taste intensity is fermentation of a microorganism, which involves producing 5'-xanthosine monophosphate and enzymatically converting the same to 5'-guanosine monophosphate. As this method is the most economical, 5'-xanthosine monophosphate is needed as much as 5'-guanosine monophosphate.

As the methods for preparing 5'-xanthosine monophosphate, (1) chemical synthesis, (2) deamination of the prepared 5-xanthosine monophosphate, (3) fermentative production by adding xanthine as a precursor in the culture medium, (4) direct fermentation of a mutant strain of a microorganism producing 5'-xanthosine monophosphate, etc. are known. Among the various methods, the direct fermentation of 5-xanthosine monophosphate by a mutant microorganism strain is the most advantageous economically. Nevertheless, research on methods for producing 5'-xanthosine monophosphate in a high yield is still in demand.

DETAILED DISCLOSURE

Technical Problem

The present inventors made extensive efforts to develop microorganisms capable of producing a high yield of 5'-xanthosine monophosphate, and as a result, they found that the production yield of 5'-xanthosine monophosphate increases when activity of a particular protein is enhanced, thereby completing the present disclosure.

Technical Solution

An object of the present disclosure is to provide a microorganism of the genus *Corynebacterium* producing 5'-xanthosine monophosphate, in which activity of a protein comprising an amino acid sequence of SEQ ID NO: 2 is enhanced.

Another object of the present disclosure is to provide a method for producing 5'-xanthosine monophosphate using the microorganism.

Advantageous Effects

The microorganism of the genus *Corynebacterium* of the present disclosure has enhanced activity of a protein that exports 5-xanthosine monophosphate, thereby having increased 5'-xanthosine monophosphate production, and this can significantly contribute to reduction of the production cost of 5-xanthosine monophosphate.

BEST MODE

Hereinbelow, the present disclosure is described in more detail. Meanwhile, each description and exemplary embodiment disclosed in the present disclosure can be applied to other descriptions and exemplary embodiments. That is, all combinations of the various elements disclosed in the present disclosure fall within the scope of the present disclosure. Additionally, the scope of the present disclosure cannot be construed as being limited by the specific description below.

As an aspect to achieve the above objects, the present disclosure provides a microorganism of the genus *Corynebacterium* producing 5'-xanthosine monophosphate, in which activity of a protein comprising an amino acid sequence of SEQ ID NO: 2 is enhanced.

As used herein, the term "5'-xanthosine monophosphate" refers to a compound named 5'-xanthylic acid, xanthosine, etc. In the present disclosure, the 5'-xanthosine monophosphate can be interchangeably used with "XMP".

As used herein, the term "protein comprising an amino acid sequence of SEQ ID NO: 2" refers to a protein endogenously present in a microorganism of the genus *Corynebacterium*, encoded by a major facilitator superfamily transporter (MFS transporter) gene exporting 5'-xanthosine monophosphate from the microorganism. Specifically, it may be an MFS transporter protein including the amino acid sequence of SEQ ID NO: 2, which is endogenously present in the microorganism of the genus *Corynebacterium*. Further, the protein may be a protein consisting of or composed of the amino acid sequence of SEQ ID NO: 2, but is not limited thereto. The MFS transporter protein in the present disclosure may be called "xmpE" or "xmpE protein".

As used herein, "protein comprising an amino acid sepuence of a particular SEQ ID NO", as long as it has activity identical or corresponding to a protein including the same SEQ ID NO, may include an addition of a sequence which has no alter the function of the proteinat the front of the end of the amino acid sequence; a naturally occurring mutation; or a silent mutation thereof. In the case of proteins having such sequence addition or mutation, it is apparent that they are also included within the scope of the present disclosure.

Further, the protein of the present disclosure may comprise the amino acid sequence of SEQ ID NO: 2, but also that having at least 60% homology or identity to SEQ ID NO: 2. The protein comprising the amino acid sequence having at least 60% homology or identity to SEQ ID NO: 2 may be a protein including an amino acid sequence having at least 60%, specifically 70%, more specifically 80%, even more specifically 83%, 84%, 85%, 88%, 90%, 93%, 95%, or 97% homology or identity to SEQ ID NO: 2. The amino acid sequence having the homology or identity may exclude that having 100% identity from said range or be that having identity of less than 100%. It is obvious that as long as the amino acid sequence, as a sequence having the sequence homology or identity, substantially has biological activity identical or corresponding to that of SEQ ID NO: 2, it is included in the scope of the present disclosure even if part of the sequence has deletion, modification, substitution, or addition of an amino acid sequence.

Additionally, a nucleotide sequence of a gene encoding the protein comprising the amino acid sequence of SEQ ID NO: 2 can be obtained from a known database such as NCBI GenBank, but is not limited thereto. Specifically, the protein comprising the amino acid sequence of SEQ ID NO: 2 may be encoded by a gene including a nucleotide sequence of SEQ ID NO: 1, as well as a gene consisting of or composed of the nucleotide sequence of SEQ ID NO: 1, but is not limited thereto.

Further, the nucleotide sequence of SEQ ID NO: 1 may include not only the nucleotide sequence of SEQ ID NO: 1 itself but also a nucleotide sequence having at least 80% homology or identity to SEQ ID NO: 1.

Specifically, any nucleotide sequence capable of encoding an amino acid sequence having at least 80% homology or identity to SEQ ID NO: 2 is included within the scope of the present disclosure, but the protein may be encoded by a gene including a nucleotide sequence having at least 80%, specifically 83%, 84%, 85%, 88%, 90%, 93%, 95%, or 97% homology or identity to SEQ ID NO: 1. However, it is obvious that a nucleotide sequence is included within the scope of the present disclosure without limitation as long as it encodes a protein having activity corresponding to that of the protein including the amino acid sequence of SEQ ID NO: 2.

Additionally, it is obvious that due to genetic code degeneracy, a polynucleotide which can be translated to a protein including the same amino acid sequence or a protein having homology or identity thereto can be included within the scope of the present disclosure. Further, a probe which can be prepared from a known gene sequence, e.g., any sequence encoding a protein having activity of a protein including the amino acid sequence of SEQ ID NO: 2 by hybridizing the whole or a part of the nucleotide sequence with its complement sequence under stringent conditions can be included without limitation. The "stringent conditions" refer to conditions enabling specific hybridization between polynucleotides. The conditions are described in detail in the reference (J. Sambrook et al., Molecular Cloning, A Laboratory Manual, 2nd Edition, Cold Spring Harbor Laboratory press, Cold Spring Harbor, N.Y., 1989); for example, a condition in which genes having high homology or identity of at least 40%, specifically 85%, specifically 90%, more specifically 95%, more specifically 97%, and particularly specifically 99% are hybridized and those having lower homology or identity are not hybridized; or a condition of conventional Southern hybridization, that is, washing once, specifically two to three times at a temperature and salt concentration equivalent to 60° C., 1×SSC, 0.1% SDS, specifically 60° C., 0.1×SSC, 0.1% SDS, more specifically 68° C., 0.1×SSC, 0.1% SDS. Although the hybridization may allow mismatch between bases depending on the degree of stringency, it requires two nucleic acids to have a complementary sequence to each other. As used herein, the term "complementary" is used for describing the relation between nucleotide bases capable of hybridization with each other. With respect to DNA, for example, adenosine is complementary to thymine, and cytosine is complementary to guanine. Accordingly, the present disclosure may also include an isolated nucleic acid fragment complementary to not only a substantially similar nucleic acid sequence but also the entire sequence.

Specifically, the polynucleotide having homology or identity can be detected using a hybridization condition including a hybridization step at a $T_m$ value of 55° C. and the above-described conditions. Further, the $T_m$ value may be 60° C., 63° C., or 65° C., but is not limited thereto and can be appropriately adjusted by a person skilled in the art.

An appropriate degree of stringency of polynucleotide hybridization is dependent on the length and degree of complementarity of the polynucleotide, and variables are well known in the corresponding technical field (see Sambrook et al., supra, 9.50-9.51, 11.7-11.8).

As used herein, the term "homology" refers to the degree of identity between two given amino acid sequences or nucleotide sequences and can be expressed as a percentage. In the present specification, the homologous sequence having the same or similar activity with the given amino acid sequence or polynucleotide sequence may be indicated in terms of "% homology".

As used herein, the term "identity" refers to the degree of sequence relatedness between amino acid or nucleotide sequences, and in some cases, it may be determined by a match between the strings of such sequences.

The terms "homology" and "identity" are often used interchangeably with each other. Sequence homology or identity of conserved polynucleotides or polypeptides may be determined by standard alignment algorithms and used with a default gap penalty established by a program being used. Substantially, homologous or identical polynucleotides or polypeptides are generally expected to hybridize under moderate or high stringency, along at least about 50%, 60%, 70%, 80%, or 90% of the entire length of all or target polynucleotides or polypeptides. Polynucleotides that contain degenerate codons instead of codons in the hybridizing polypeptides are also considered.

Whether any two polynucleotide or polypeptide sequences have a homology or identity of, for example, at least 50%, 55%, 60%, 65% 70%, 75%, 80%, 85%, 90%, 95%, 96%, 97%, 98%, or 99% may be determined using a known computer algorithm such as the "FASTA" program (e.g., Pearson et al., (1988) *Proc. Natl. Acad. Sci. USA* 85: 2444) using default parameters. Alternatively, it may be determined using the Needleman-Wunsch algorithm (Needleman and Wunsch, 1970, *J. Mol. Biol.* 48: 443-453), which is performed in the Needleman program of the EMBOSS package (EMBOSS: The European Molecular Biology Open Software Suite, Rice et al., 2000, *Trends Genet.* 16: 276-277) (preferably, version 5.0.0 or later). (Including GCG program package (Devereux, J., et al.,

*Nucleic Acids Research* 12: 387 (1984)), BLASTP, BLASTN, FASTA (Atschul, [S.] [F.,] [ET AL., *J MOLEC BIOL* 215]: 403 (1990); Guide to Huge Computers, Martin J. Bishop, [ED.,] Academic Press, San Diego, 1994, and [CARILLO ETA/.](1988) SIAM *J Applied Math* 48: 1073). For example, the homology or identity may be determined using BLAST or ClustalW of the National Center for Biotechnology Information (NCBI).

The homology or identity of polynucleotide or polypeptide may be determined by comparing sequence information as published (e.g., Smith and Waterman, *Adv. Appl. Math* (1981) 2:482), for example, using the GAP computer program as disclosed in Needleman et al. (1970), J Mol Bio1.48: 443. In summary, the GAP program defines the homology or identity as a value obtained by dividing the number of similarly aligned symbols (i.e., nucleotides or amino acids) by the total number of symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to a relevance between polypeptides or polynucleotides.

The microorganism of the genus *Corynebacterium* producing 5'-xanthosine monophosphate in the present disclosure may have enhanced activity of the protein including the amino acid sequence of SEQ ID NO: 2.

The enhancement of activity of the protein including the amino acid sequence of SEQ ID NO: 2 can be interchangeably used with the enhancement of activity of xmpE or that of a protein encoded by a gene including the nucleotide sequence of SEQ ID NO: 1.

As used herein, the term "enhanced activity of a protein comprising the amino acid sequence of SEQ ID NO: 2" refers to enhanced expression of the protein compared to its parent strain or that of the protein including the amino acid sequence of SEQ ID NO: 2 compared to an unmodified strain; enhanced activity thereof with equivalent expression; or enhanced activity and expression thereof. The term also refers to enhanced activity of the protein compared to its endogenous activity, and enhanced expression or activity of xmpE compared to the parent strain or unmodified strain thereof.

In the present disclosure, the enhancement of protein activity can be achieved by applying various methods known in the art. For example, the enhancement of activity may be achieved by increasing the copy number of polynucleotides encoding the protein, enhancing the promoter activity, substitution of a start codon, or a combination thereof; specifically, 1) increasing the copy number of polynucleotide encoding the protein; 2) modifying a sequence of an expression regulator (promoter, operator, etc.) so as to increase the expression of the polynucleotide; 3) modifying a sequence of the gene (start codon, etc.) on a chromosome so as to enhance the protein activity, or a combination thereof, but is not limited thereto.

Specifically, with respect to the enhancement of the protein activity, the method for modifying a sequence of an expression regulator can be achieved by applying various methods known in the art. For example, the modification can be carried out to enhance the activity of the expression regulator sequence by inducing a modification by deletion, insertion, or non-conservative or conservative substitution, or a combination thereof in the regulatory sequence; or substituting the nucleotide sequence with a nucleotide sequence having more enhanced activity. The expression regulator includes a promoter, an enhancer, an operator, a ribosome-binding site, and a sequence which regulates termination of transcription and translation, but is not limited thereto.

Additionally, the method for modifying the sequence of the gene can be carried out to enhance the protein activity by inducing a modification by deletion, insertion, or non-conservative or conservative substitution, or a combination thereof in the sequence; or substituting the gene sequence with a modified gene sequence having more enhanced activity, but is not limited thereto.

In a specific exemplary embodiment, the enhancement of the protein activity can be achieved by increasing the copy number of xmpE; replacing a promoter of xmpE with another promoter having enhanced activity; substituting the start codon of xmpE; or a combination thereof.

As used herein, the term "vector" refers to a DNA construct comprising the nucleotide sequence of the polynucleotide encoding the target protein operably linked to the proper regulatory sequence to express the target protein in the proper host. The regulatory sequence can include the promoter which can initiate transcription, any operator sequence to control the transcription, the sequence to encode the appropriate mRNA ribosome binding site, and the sequence to control the termination of transcription and translation. The vector may be transfected into a suitable host, and then may be replicated or function independently from the host genome, and may be integrated into the genome itself.

As used herein, the term "transformation" refers to the introduction of a vector including a polynucleotide encoding a target protein into a host cell so that the protein encoded by the polynucleotide can be expressed in the host cell. As long as it can be expressed in the host cell, the transformed polynucleotide can be either integrated into and placed in the chromosome of the host cell or located extrachromosomally. Further, the polynucleotide includes DNA and RNA encoding the target protein. The polynucleotide may be introduced in any form as long as it can be introduced into the host cell and expressed therein. For example, the polynucleotide may be introduced into the host cell in the form of an expression cassette, which is a polynucleotide construct including all elements required for its autonomous expression. The expression cassette may include a promoter operably linked to the gene, a transcription termination signal, a ribosome-binding site, and a translation termination signal. The expression cassette may be in the form of a self-replicable expression vector. In addition, the polynucleotide may be introduced into the host cell as is and operably linked to a sequence required for the expression in the host cell.

As used herein, the term "microorganism producing 5'-xanthosine monophosphate" or "microorganism having abilities to produce 5'-xanthosine monophosphate" refers to a microorganism naturally having abilities to produce 5'-xanthosine monophosphate or a microorganism in which ability to produce 5'-xanthosine monophosphate is endowed to a parent strain having no ability to produce 5'-xanthosine monophosphate. Specifically, it may be a microorganism having abilities to produce 5'-xanthosine monophosphate, in which the activity of a protein including the amino acid sequence of SEQ ID NO: 2 or xmpE protein is enhanced.

Further, considering the object of the present disclosure, the ability to produce 5'-xanthosine monophosphate of the microorganism may be improved/enhanced due to the enhancement of 5-xanthosine monophosphate-exporting ability.

Specifically, the terms "ability to produce" and "exporting ability" can be interchangeably used. Further, the microorganism can be interchangeably used with "microorganism exporting 5'-xanthosine monophosphate" or "microorganism having 5'-xanthosine monophosphate-exporting ability". It may refer to a microorganism naturally having 5'-xanthosine monophosphate-exporting ability or a microorganism in which 5'-xanthosine monophosphate-exporting ability is endowed to a parent strain having no 5'-xanthosine monophosphate-exporting ability.

Specifically, the microorganism of the genus *Corynebacterium* producing 5'-xanthosine monophosphate may be *Corynebacterium stationis* or *Corynebacterium glutamicum*, or *Corynebacterium* ammoniagenes; and more specifically may be *Corynebacterium stationis*, but is not limited thereto.

As another aspect, the present disclosure provides a method for producing 5'-xanthosine monophosphate, comprising culturing the microorganism of the genus *Corynebacterium* in a culture medium; and recovering the 5'-xanthosine monophosphate from the microorganism or the culture medium.

The microorganism and 5'-xanthosine monophosphate according to the present disclosure are the same as previously described.

The microorganism of the genus *Corynebacterium* in the present disclosure may be *Corynebacterium stationis*, but is not limited thereto.

With respect to the method of the present disclosure, the microorganism of the genus *Corynebacterium* may be cultured using any culturing conditions and methods known in the art.

As used herein, the term "culture" refers to cultivation of the microorganism under moderately artificially controlled environmental conditions. The culturing process of the present disclosure can be carried out according to a suitable culture medium and culture conditions known in the art. Further, the culture method includes a batch culture, a continuous culture, and a fed-batch culture; specifically, a batch process or a fed batch or a repeated fed batch process can be continuously cultured, but the culture method is not limited thereto.

The medium used for culture shall meet the requirements of specific strains in a proper manner. The culture medium for the microorganism of the genus *Corynebacterium* is known in the art (e.g., Manual of Methods for General Bacteriology by the American Society for Bacteriology, Washington D.C., USA, 1981).

Specifically, sugar sources which may be used for the medium include saccharides and carbohydrates such as glucose, saccharose, lactose, fructose, maltose, starch, cellulose, etc.; oils and fats such as soybean oil, sunflower oil, castor oil, coconut oil, etc.; fatty acids such as palmitic acid, stearic acid, linoleic acid, etc.; glycerol; alcohols such as ethanol; and organic acids such as acetic acid. These substances can be used individually or as a mixture, but are not limited thereto.

Carbon sources which may be used may be crude sucrose or glucose, or molasses containing a large amount of sucrose; and specifically may be purified glucose, but are not limited thereto. Other various carbon sources may be used.

Nitrogen sources which may be used include peptone, yeast extract, beef extract, malt extract, corn steep liquor, soybean meal, and urea or inorganic compounds, for example, ammonium sulfate, ammonium chloride, ammonium phosphate, ammonium carbonate, and ammonium nitrate. The nitrogen sources can also be used individually or as a mixture, but are not limited thereto.

Phosphate sources which may be used include potassium dihydrogen phosphate, dipotassium hydrogen phosphate, or corresponding sodium-containing salts.

Further, the culture medium may contain metallic salts such as magnesium sulfate or iron sulfate. In addition to the above materials, essential growth substances such as amino acids and vitamins may be used. Appropriate precursors may also be used for the culture medium. The raw materials described above may be added batch-wise or continuously to an incubator in an appropriate manner.

A pH of the culture medium may be adjusted by using a basic compound such as sodium hydroxide, potassium hydroxide, and ammonia; or an acidic compound such as phosphoric acid and sulfuric acid in an appropriate manner. Additionally, foam formation may be suppressed by using an antifoaming agent such as fatty acid polyglycol ester. Oxygen or an oxygen-containing gas (e.g., air) may be injected into the culture medium to maintain an aerobic condition.

Specifically, the culturing temperature is normally 30° C. to 37° C., more specifically 32° C. to 33° C. The culturing may continue until a desired amount of 5'-xanthosine monophosphate is obtained, but specifically may be performed for 40 hours to 120 hours.

The separation of 5'-xanthosine monophosphate from the culture may be carried out by a conventional method known in the art; e.g., centrifugation, filtration, ion-exchange chromatography, crystallization, etc. For example, the culture may be centrifuged at a low speed to remove biomass, and then, the obtained supernatant may be separated through ion-exchange chromatography. However, the separation is not limited thereto.

The recovery step may further include a purifications process.

[Mode for Invention]

Hereinafter, the present disclosure will be described in more detail with reference to the following exemplary embodiments. However, these Examples are for illustrative purposes only, and the present disclosure is not intended to be limited by these Examples.

Example 1: Discovery of 5'-xanthosine Monophosphate (XMP)-Exporting Protein

To identify membrane protein of *Corynebacterium* involved in XMP export, a genomic DNA library of *Corynebacterium stationis* (ATCC6872) was prepared. A genomic DNA of ATCC6872 strain (i.e., wild type of *Corynebacterium stationis*) was extracted using G-spin Total DNA Extraction Minin Kit by Intron (Cat. No. 17045) according to the protocol provided therein. The membrane protein library was prepared using the extracted genomic DNA as a template.

To investigate which protein has the export function, the prepared genomic DNA library was introduced into the *Corynebacterium* KCCM-10530 strain used as a parent strain in KR XMP was then additionally added to the minimal culture medium containing 1.7% agar to establish a screening condition in which the KCCM-10530 strain shows growth inhibition. The KCCM-10530 strain was transformed by electroporation with A genomic library plasmid of a membrane protein of ATCC6872 strain, and colonies were selected which normally grow in a condition where an excessive amount of XMPs are added to the culture medium. A plasmid was obtained from the selected colony and its nucleotide sequence was analyzed by a nucleotide sequence analysis method. One type of membrane protein involved in removing the growth inhibition under the condition of an excessive amount of XMP added was identified from the experiment above.

The *Corynebacterium* membrane protein was confirmed to have the nucleotide sequence of SEQ ID NO: 1 and the amino acid sequence of SEQ ID NO: 2 (NCBI GenBank: NZ_CP014279.1, WP 066795121, MFS transporter). The membrane protein is known as an MFS transporter, but its function is not clearly identified. Besides, it is not known to have the function of exporting XMP. In the present disclosure, the membrane protein is named as "xmpE".

Example 2: Identification of xmpE

Example 2-1: Preparation of xmpE-Deficient Vector

A Deficient vector was prepared to confirm whether the XMP-exporting ability decreases when xmpE, the protein involved in removing growth inhibition due to the XMP identified in Example 1, is deleted from the XMP-producing strain.

A gene fragment for the vector preparation was obtained by PCR using the genomic DNA of the ATCC6872 strain as a parent strain. Specifically, the PCR was performed for the xmpE using primers of SEQ ID NOS: 3 and 4. The primers that were used were prepared based on the information on *Corynebacterium stationis* (ATCC6872) genes registered in the National Institutes of Health (NIH) GenBank (NCBI Genbank: NZ_CP014279.1) and the surrounding nucleotide sequence thereof.

The PCR was performed under the following conditions: denaturation at 94° C. for 5 minutes; 25 cycles of denaturation at 94° C. for 30 seconds, annealing at 52° C. for 30 seconds, and polymerization at 72° C. for 1 minute. Final polymerization was then performed at 72° C. for 5 minutes. As an xmpE gene fragment amplified using the primers of SEQ ID NOS: 3 and 4, a polynucleotide template of about 1.0 kbp was obtained. The obtained gene fragment was cloned using a T vector (Solgent) to obtain a TOPO-AxmpE vector.

Example 2-2: Preparation of xmpE-Deficient Strain

The KCCM-10530 strain was transformed by electroporation with the vector prepared in example 2-1 (using the transformation method according to Appl. Microbiol. Biotechnol. (1999) 52:541-545), and the strain having the vector inserted on a chromosome due to the homologous sequence recombination was selected from a culture medium containing 25 mg/L kanamycin. The selected xmpE-deficient strain was named as "KCCM-10530 AxmpE", and its ability to produce XMP was evaluated.

The parent strain *Corynebacterium stationis* KCCM-10530 and the strain KCCM-10530_ΔxmpE were inoculated into a 14 mL tube including 3 mL of the seed culture medium below and cultured at 30° C. for 24 hours with shaking at 170 rpm. Then, the seed cultures were added in an amount of 0.7 mL to 32 mL of the following production culture medium (24 mL of main culture medium+8 mL of additional sterile culture medium) in respective 250 mL corner-baffle flasks, followed by culturing at 30° C. for 72 hours with shaking at 170 rpm. HPLC analysis was performed to measure the amount of XMP produced after completion of the culture. The constitution of the culture medium and the result of XMP concentrations in the culture medium are as shown in Table 1 below.

XMP Minimal Culture Medium
  glucose 2%, sodium sulfate 0.3%, monopotassium phosphate 0.1%, dipotassium phosphate 0.3%, magnesium sulfate 0.3%, calcium chloride 10 mg/L, iron sulfate 10 mg/L, zinc sulfate 1 mg/L, manganese chloride 3.6 mg/L, L-cysteine 20 mg/L, calcium pantothenate 10 mg/L, thiamine hydrochloride 5 mg/L, biotin 30 µg/L, adenine 20 mg/L, guanine 20 mg/L, pH 7.3

XMP Nutritional Culture Medium
  peptone 1%, beef extract 0.5%, sodium chloride 0.25%, yeast extract 1%, urea 0.3%, adenine 50 mg/L, guanine 50 mg/L, agar 2%, pH 7.2

XMP Flask Seed Culture Medium
  glucose 20 g/L, peptone 10 g/L, yeast extract 10 g/L, sodium chloride 2.5 g/L, urea 3 g/L, adenine 150 mg/L, guanine 150 mg/L, pH 7.0

XMP Flask Production Culture Medium (Main Culture Medium) glucose 50 g/L, magnesium sulfate 10 g/L, calcium chloride 100 mg/L, iron sulfate 20 mg/L, manganese sulfate 10 mg/L, zinc sulfate 10 mg/L, copper sulfate 0.8 mg/L, histidine 20 mg/L, cysteine 15 mg/L, beta-alanine 15 mg/L, biotin 100 µg/L, thiamine 5 mg/L, adenine 50 mg/L, guanine 25 mg/L, niacin 5 mg/L, pH 7.0

XMP Flask Production Culture Medium (Additional Sterile Culture Medium)
  monopotassium phosphate 18 g/L, dipotassium phosphate 42 g/L, urea 7 g/L, ammonium sulfate 5 g/L

TABLE 1

| Strain No. | XMP (g/L) | Yield (%) |
| --- | --- | --- |
| KCCM-10530 | 11.8 | 23.6 |
| KCCM-10530-ΔxmpE | 1.6 | 3.2 |

The XMP concentrations in the culture media of the parent strain KCCM-10530 and the xmpE-deficient strain KCCM-10530-AxmpE were compared; as a result, as shown in Table 1 above, the XMP concentration of the KCCM-10530-AxmpE strain decreased at least about 10 g/L compared to the parent strain under the same conditions.

Accordingly, xmpE was confirmed to be a protein involved in the XMP export.

Example 3: Enhancement of xmpE Protein Activity

The activity of the xmpE protein in the strain was enhanced according to the following Examples, and the strain with enhanced xmpE activity was examined with respect to whether its ability to produce/export XMP was increased.

Example 3-1: Increase in Copy Number of xmpE

Example 3-1-1: Preparation of Vector for Increasing Copy Number of xmpE

In order to confirm whether the XMP-exporting ability increases when the activity of xmpE, which is predicted to be involved in the XMP-exporting ability, is enhanced, a vector was prepared for enhancing an xmpE gene. Using a method for increasing the copy number as the enhancement method, the following experiment was performed.

The gene fragment for preparing the vector was obtained through PCR using genomic DNA of the ATCC6872 strain as a template. Specifically, the xmpE gene was amplified so as to contain upstream 484 bp of the xmpE gene using a pair of the primers of SEQ ID NOS: 5 and 6. The amplified xmpE gene fragment was treated with restriction enzymes XbaI and SpeI. The cloning was performed on the XbaI site of pDZ vector (KR patent No. 10-0924065 and International Publication No. 2008-033001) to prepare a pDZ-xmpE vector. PCR was then performed on the xmpE gene using a pair of the primers of SEQ ID NOS: 6 and 7 in order to prepare the vector containing two copies. Each DNA fragment thus obtained was cleaved with the DNA restriction enzyme SpeI, and cloned into the pDZ-xmpE vector cleaved by the DNA restriction enzyme XbaI so as to prepare a vector. The vector containing two copies of the xmpE gene was named as "pDZ-xmpEX2".

Example 3-1-2: Evaluation of Ability to Produce XMP of the Strain Having an Increased Copy Number of xmpE The KCCM-10530 strain was transformed by electroporation with the pDZ-xmpEX2 vector prepared in Example 3-1-1 (using the transformation method according to Appl. Microbiol. Biotechnol. (1999) 52:541-545), and the strain having the vector inserted on the chromosome due to the homologous sequence recombination was selected from a culture medium containing 25 mg/L kanamycin. The strain into which a target gene is inserted was selected by secondary crossover of the selected primary strain. The successful insertion of the gene of the ultimate transformed strain was confirmed by PCR using a pair of the primers of SEQ ID NOS: 8 and 9. The selected strain with an increased copy number of xmpE was named as "KCCM-10530-xmpEX2", and its ability to produce XMP was evaluated.

In order to measure the ability to produce XMP of the strain, the same method as in Example 2-2 was used. HPLC analysis was performed to measure the amount of XMP produced after completion of the culture, and the result is as shown in Table 2 below.

TABLE 2

| Strain No. | XMP (g/L) | Yield (%) |
| --- | --- | --- |
| KCCM-10530 | 11.8 | 23.6 |
| KCCM-10530-xmpEX2 | 13.1 | 26.1 |

The XMP concentrations in the culture media of the parent strain *Corynebacterium stationis* KCCM-10530 and the KCCM-10530-xmpEX2 strain having an increased copy number of xmpE were compared; as a result, as shown in Table 2 above, the XMP concentration of the KCCM-10530-xmpEX2 strain was 1.3 g/L, indicating a concentration increase of about 11% compared to the parent strain under the same conditions.

This can be understood as a very meaningful result through which such increase in the amount of XMP produced is confirmed to be due to the enhanced xmpE protein activity.

Example 3-2: Enhancement of xmpE Expression Through Substitution of Promoter

Example 3-2-1: Preparation of Vector for Replacing xmpE Promoter

In order to confirm whether the XMP-exporting ability increases when the activity of xmpE, which is predicted to be involved in the XMP-exporting ability, is enhanced, a vector was prepared in which the promoter of xmpE gene is substituted with a promoter capable of strong expression. A gene fragment for preparing the vector was obtained by PCR using genomic DNA of the ATCC6872 strain as a template.

Pcj7, which is reported to be strongly expressed in *Corynebacterium stationis* in KR patent No. 10-0620092, was used as a promoter.

In order to amplify a fragment of Pcj7 gene, a pair of the primers of SEQ ID NOS: 10 and 11 was used using the genomic DNA of the ATCC6872 strain as a template. Each xmpE gene was amplified by PCR using a pair of the primers of SEQ ID NOS: 12 and 13; and 14 and 15, respectively. The PCR reaction was performed under the following conditions: denaturation at 94° C. for 5 minutes; 25 cycles of denaturation at 94° C. for 30 seconds, annealing at 52° C. for 30 seconds, and polymerization at 72° C. for 1 minute. Final polymerization was then performed at 72° C. for 5 minutes. A 2.3 kbp polynucleotide template was obtained by performing overlapping polymerase chain reaction using the three amplified gene fragments Pcj7, xmpE-1, and xmpE-2 as templates. The obtained gene fragment was cleaved by a restriction enzyme XbaI, and was cloned into the linear pDZ vector cleaved with XbaI using T4 ligase to prepare a "pDZ-Pcj7/xmpE" vector.

Example 3-2-2: Preparation of Strain Having Substituted xmpE Promoter and Evaluation of its Ability to Produce XMP The KCCM10530 strain was transformed by electroporation with The pDZ-Pcj7/xmpE vector prepared in Example 3-2-1 (using the transformation method according to Appl. Microbiol. Biotechnol. (1999) 52:541-545), and the strain having the vector inserted on the chromosome due to the homologous sequence recombination was selected from a culture medium containing 25 mg/L kanamycin. The strain into which a target gene is enhanced was selected by secondary crossover of the selected primary strain. The successful insertion of the gene promoter of the ultimate transformed strain was confirmed by PCR using a pair of the primers of SEQ ID NOS: 16 and 17. The strain in which the promoter is substituted with a stronger promoter was named as "KCCM-10530-Pcj7/xmpE", and its ability to produce XMP was evaluated.

In order to measure the ability to produce XMP of the strain, the same method as in Example 2-2 was used. HPLC analysis was performed to measure the amount of XMP produced after completion of the culture, and the result is as shown in Table 3 below.

TABLE 3

| Strain No. | XMP (g/L) | Yield (%) |
| --- | --- | --- |
| KCCM-10530 | 11.8 | 23.6 |
| KCCM-10530-Pcj7/xmpE | 12.5 | 25.0 |

The XMP concentrations in the culture media of the parent strain *Corynebacterium stationis* KCCM-10530 and the KCCM-10530-Pcj7/xmpE strain having an enhanced xmpE expression due to the stronger promoter were compared; as a result, as shown in Table 3 above, the XMP concentration of the KCCM-10530-Pcj7/xmpE strain was 0.7 g/L, indicating a concentration increase of about 6% compared to the parent strain under the same conditions.

This can be understood as a very meaningful result through which such increase in the amount of XMP produced is confirmed to be due to the enhanced xmpE protein activity.

Example 3-3: Substitution of Start Codon of xmpE

Example 3-3-1: Preparation of Vector for Substituting Start Codon of xmpE

In order to confirm whether the XMP-excreting ability increases when the expression of the xmpE protein, which is predicted to be involved in the XMP-excreting ability, is enhanced, a vector was prepared in which the start codon gtg is substituted with atg. A gene fragment for preparing the vector was obtained by PCR using a genomic DNA of the ATCC6872 strain as a template. In order to prepare a vector having the start codon gtg substituted with atg, two gene fragments A and B were obtained using pairs of the primers of SEQ ID NOS: 18 and 19, and 20 and 21, respectively. The PCR reaction was performed under the following conditions: 25 cycles of denaturation at 94° C. for 5 minutes; denaturation at 94° C. for 30 seconds; annealing at 52° C. for 30 seconds; and polymerization at 72° C. for 1 minute. Final polymerization was then performed at 72° C. for 5 minutes. As a result, about 0.7 kbp and 1 kbp polynucleotides were obtained for fragments A and B, respectively. Using the two fragments as templates, PCR was conducted using a pair of the primers of SEQ ID NOS: 18 and 21 to obtain a PCR resultant of about 1.7 kbp (hereinafter, "gla fragment"). The polymerization was performed under the following conditions: 25 cycles of denaturation at 94° C. for 5 minutes; denaturation at 94° C. for 30 seconds; annealing at 55° C. for 30 seconds; and polymerization at 72° C. for 120 seconds. Final polymerization was then performed at 72° C. for 7 minutes.

The obtained gene fragment was cleaved by a restriction enzyme XbaI, and was cloned into the linear pDZ vector cleaved with XbaI using T4 ligase to prepare a "pDZ-xmpE (gla)" vector.

Example 3-3-2: Preparation of Strain Having Substituted xmpE Start Codon and Evaluation of its Ability to Produce XMP The KCCM-10530 strain was transformed by electroporation with the pDZ-xmpE(gla) vector prepared in Example 3-3-1 (using the transformation method according to Appl. Microbiol. Biotechnol. (1999) 52:541-545), and the strain having the vector inserted on the chromosome due to the homologous sequence recombination was selected from a culture medium containing 25 mg/L kanamycin. The strain into which a target gene is enhanced was selected by secondary crossover of the selected primary strain. The successful insertion of the gene promoter of the ultimate transformed strain was confirmed by PCR using a pair of the primers of SEQ ID NOS: 18 and 21, followed by analyzing the nucleotide sequence substituted by a nucleotide sequence analysis method. The selected strain in which xmpE start codon is substituted with atg was named as CJX1662, and its ability to produce XMP was evaluated.

In order to measure the ability to produce XMP of the strain, the same method as in Example 2-2 was used. HPLC analysis was performed to measure the amount of XMP produced after completion of the culture, and the result is as shown in Table 4 below.

TABLE 4

| Strain No. | XMP (g/L) | Yield (%) |
|---|---|---|
| KCCM-10530 | 11.8 | 23.6 |
| CJX1662 | 14.1 | 28.2 |

The XMP concentrations in the culture media of the parent strain *Corynebacterium stationis* KCCM-10530 and the CJX1662 strain having the substituted start codon of xmpE were compared; as a result, as shown in Table 4 above, the XMP concentration of the CJX1662 strain was 2.3 g/L, indicating a concentration increase of about 20% compared to the parent strain under the same conditions.

This can be understood as a very meaningful result through which such increase in the amount of XMP produced is confirmed to be due to the enhanced xmpE protein activity.

Further, the CJX1662 strain prepared above was deposited at the Korean Culture Center of Microorganisms (KCCM), an international depositary authority under the Budapest Treaty on Apr. 11, 2018, as Accession No. KCCM12248P.

Example 3-4 Preparation of Strain Having Enhanced xmpE Based on Wild-Type XMP-Producing Cell Line Example 3-4-1: Preparation of Strain Having Enhanced xmpE Based on Wild-Type XMP-Producing Cell Line A strain having ability to produce XMP productivity was prepared by weakening activities of adenylosuccinate synthetase and XMP dehydrogenase, which belong to the XMP decomposition pathways, in a wild-type ATCC6872 strain. In order to attenuate the activities of the two enzymes, a strain was prepared in which 'a', the first nucleotide of the nucleotide sequence of purA and guaA, the genes respectively encoding the two enzymes, is substituted with 't'. More specifically, the strain prepared by weakening the expression of the two genes in the ATCC6872 strain was named as CJX1663.

The prepared CJX1663 strain was transformed by electroporation with the pDZ-xmpE(gla) vector prepared in Example 3-3-2, and the strain having the vector inserted on the chromosome due to the homologous sequence recombination was selected from a culture medium containing 25 mg/L kanamycin. The strain into which a target gene is enhanced was selected by secondary crossover of the selected primary strain. The successful insertion of the gene promoter of the ultimate transformed strain was confirmed by PCR using a pair of the primers of SEQ ID NOS: 18 and 21.

The strain in which the selected xmpE start codon is substituted with atg was named as "CJX1663_xmpE(gla)", and its ability to produce XMP was evaluated.

HPLC analysis was performed to measure the amount of XMP produced after completion of the culture, and the result is as shown in Table 5 below.

TABLE 5

| Strain No. | XMP (g/L) | Yield (%) |
|---|---|---|
| CJX1663 | 2.1 | 4.2 |
| CJX1663_xmpE(g1a) | 2.8 | 5.6 |

The XMP concentrations in the culture media of the parent strain *Corynebacterium stationis* CJX1663 and the CJX1663_xmpE(gla) strain having the substituted start codon of xmpE were compared; as a result, as shown in Table 5 above, the XMP concentration of the CJX1663_xmpE(gla) strain was 2.8 g/L, indicating a concentration increase of about 33% compared to the parent strain under the same conditions.

It was confirmed from the result that by enhancing the activity of the protein (xmpE) of the present disclosure, which exports 5'-xanthosine monophosphate, the XMP productivity can be increased.

Meanwhile, the primer sequences used in the present disclosure are as shown in Table 6.

TABLE 6

| SEQ ID NO | Sequence |
|---|---|
| 3 | GTCAAACTCTTTACGCCGACG |
| 4 | CGACAACACCAACAGATACTGC |
| 5 | ATGCTCTAGACTAGATCTTCTCGACGGGCAG |
| 6 | ATGATACTAGTCCTTGGGGACTTCGCGTGTCG |
| 7 | ATGATACTAGTCTAGATCTTCTCGACGGGCAG |
| 8 | TTCGGCTCAGCATTTTCCAC |
| 9 | CAATAGTGGTCGCGATGACG |
| 10 | GCAGTAAGGAGAATCAGAAACATCCCAGCGCTACTA |

TABLE 6-continued

| SEQ ID NO | Sequence |
|---|---|
| 11 | ACCTCTTCGGTTGTGTGCACGAGTGTTTCCTTTCGTTGGG |
| 12 | ATGCTCTAGATCCAGTGTGGTTAAGAAGTCG |
| 13 | CGCTGGGATGTTTCTGATTCTCCTTACTGCAGT |
| 14 | GTACCCAACGAAAGGAAACACTCGTGCACACAACCGAAGAGGT |
| 15 | ATGCTCTAGATTATTGAGCCAGAACCATGG |
| 16 | CTAGATCTTCTCGACGGGCAG |
| 17 | CAATAGTGGTCGCGATGACG |
| 18 | ATGCTCTAGATCCAGTGTGGTTAAGAAGTCG |
| 19 | GACCTCTTCGGTTGTGTGCATGATTCTCCTTACTGCAGTTA |
| 20 | TAACTGCAGTAAGGAGAATCATGCACACAACCGAAGAGGTC |
| 21 | ATGCTCTAGACTCGCTCTTGTCGACAACAC |

Those of ordinary skill in the art will recognize that the present disclosure may be embodied in other specific forms without departing from its spirit or essential characteristics. In this regard, the described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

The invention claimed is:

1. A method for producing 5'-guanosine monophosphate (GMP), comprising:
 culturing a microorganism of the genus *Corynebacterium*, wherein activity of a protein consisting of an amino acid sequence represented by SEQ ID NO: 2 is enhanced, in a culture medium;
 recovering 5'-xanthosine monophosphate from the microorganism or the culture medium; and
 converting 5'-xanthosine monophosphate to 5'-guanosine monophosphate.

2. The method of claim 1, wherein the protein is encoded by a gene consisting of a nucleotide sequence represented by SEQ ID NO: 1.

3. The method of claim 1, wherein the enhancement of activity is achieved by an increase in the number of copies of polynucleotides encoding the protein, enhancement of promoter activity, substitution of a start codon, or a combination thereof.

4. The method of claim 1, wherein the microorganism of the genus *Corynebacterium* is *Corynebacterium stationis*.

* * * * *

SEQUENCE LISTING

<160> NUMBER OF SEQ ID NOS: 21

<210> SEQ ID NO 1
<211> LENGTH: 1242
<212> TYPE: DNA
<213> ORGANISM: Corynebacterium sp.

<400> SEQUENCE: 1

```
gtgcacacaa ccgaagaggt caaactcttt acgccgacgt ttatcatggg gtgggtcgcc      60
aacttcctgc agttcttggt gttctacttc ctcatcacca cgatggcgct ctacgcaacc     120
aaggaattca gcgcatcgga aaccgaagca ggctttgccg ccagtgcgat tgttatcggt     180
gcggtctttt cccgtttggt ttccggatac attattgacc gcttcggtcg ccgcaaaatt     240
gtggtggtct ccgtcatcgc gaccactatt gcgtgcgcgc tatatatccc gatcgattct     300
ttggggctgc tctacgctga ccgcttcttc cacggtgtag cttatgcctt tgcgtgcacc     360
gcgattatgg cgatggtcca ggaactcatt ccttctgcac gccgctccga aggcactggc     420
tacctggctt tgggtaccac cgtttcggct gctatcggac cagcgctagc gctattttg      480 ctgggttctt tcaactacga agtcctcttc gttgtcgtcc tcggcatttc gattgtctct     540
ttgatcgctt cgctagtcat ctatttccgc acctccgacc cagagccaga gctggatgaa     600
aacggcaatg ctgctgagcc cattaagttc agcttcaagt ccatcattaa ccctaaagtc     660
ttgccgattg gcctcttcat gctgctggta gcctttgcct actccggcgt gatcgcacat     720
atcaacgctt ttgctgaaaa ccgcgacgtt gttactggcg caggcctatt ctttatcgct     780
tacgccatct ccatgttcgt gatgcgctcc taccttggta aattgcaaga ccgccgggc     840
```

```
gataacagcg ttatctactt tggtctcgta ttctttgtta tctcatttat cgtgctctcg    900 cttctaccg ccaactggca tgtcgttgtc gctggcgtgc tagcaggtct gggctacggc    960
accttgatgc cagctgctca agcagtatct gttggtgttg tcgacaagag cgagttcggc   1020
tcagcatttt ccaccttgtt cctttttcgtt gacctcggct tcggcttcgg cccagtcatc   1080
cttggtgcag tggtttccgc gattggctac ggttcgatgt atgcagtgct cgtcggcgtc   1140
ggcgttattg ctggcatcta ctacctgttc acccacgcac gcaccgagcg cgcaaagcac   1200
ggcgtagtca agcatgtaga aaccatggtt ctggctcaat aa                      1242
```

<210> SEQ ID NO 2
<211> LENGTH: 413
<212> TYPE: PRT
<213> ORGANISM: Corynebacterium sp.

<400> SEQUENCE: 2

```
Val His Thr Thr Glu Glu Val Lys Leu Phe Thr Pro Thr Phe Ile Met
1               5                   10                  15

Gly Trp Val Ala Asn Phe Leu Gln Phe Leu Val Phe Tyr Phe Leu Ile
            20                  25                  30

Thr Thr Met Ala Leu Tyr Ala Thr Lys Glu Phe Ser Ala Ser Glu Thr
        35                  40                  45

Glu Ala Gly Phe Ala Ala Ser Ala Ile Val Ile Gly Ala Val Phe Ser
    50                  55                  60

Arg Leu Val Ser Gly Tyr Ile Ile Asp Arg Phe Gly Arg Arg Lys Ile
65                  70                  75                  80

Val Val Val Ser Val Ile Ala Thr Thr Ile Ala Cys Ala Leu Tyr Ile
                85                  90                  95

Pro Ile Asp Ser Leu Gly Leu Leu Tyr Ala Asp Arg Phe Phe His Gly
            100                 105                 110

Val Ala Tyr Ala Phe Ala Cys Thr Ala Ile Met Ala Met Val Gln Glu
        115                 120                 125

Leu Ile Pro Ser Ala Arg Arg Ser Glu Gly Thr Gly Tyr Leu Ala Leu
    130                 135                 140

Gly Thr Thr Val Ser Ala Ala Ile Gly Pro Ala Leu Ala Leu Phe Leu
145                 150                 155                 160

Leu Gly Ser Phe Asn Tyr Glu Val Leu Phe Val Val Leu Gly Ile
                165                 170                 175

Ser Ile Val Ser Leu Ile Ala Ser Leu Val Ile Tyr Phe Arg Thr Ser
            180                 185                 190

Asp Pro Glu Pro Glu Leu Asp Glu Asn Gly Asn Ala Ala Glu Pro Ile
        195                 200                 205

Lys Phe Ser Phe Lys Ser Ile Ile Asn Pro Lys Val Leu Pro Ile Gly
    210                 215                 220

Leu Phe Met Leu Leu Val Ala Phe Ala Tyr Ser Gly Val Ile Ala His
225                 230                 235                 240

Ile Asn Ala Phe Ala Glu Asn Arg Asp Val Val Thr Gly Ala Gly Leu
                245                 250                 255

Phe Phe Ile Ala Tyr Ala Ile Ser Met Phe Val Met Arg Ser Tyr Leu
            260                 265                 270

Gly Lys Leu Gln Asp Arg Arg Gly Asp Asn Ser Val Ile Tyr Phe Gly
        275                 280                 285

Leu Val Phe Phe Val Ile Ser Phe Ile Val Leu Ser Leu Ser Thr Ala
    290                 295                 300
```

Asn Trp His Val Val Ala Gly Val Leu Ala Gly Leu Gly Tyr Gly
305                 310                 315                 320

Thr Leu Met Pro Ala Ala Gln Ala Val Ser Val Gly Val Val Asp Lys
                325                 330                 335

Ser Glu Phe Gly Ser Ala Phe Ser Thr Leu Phe Leu Phe Val Asp Leu
            340                 345                 350

Gly Phe Gly Phe Gly Pro Val Ile Leu Gly Ala Val Val Ser Ala Ile
        355                 360                 365

Gly Tyr Gly Ser Met Tyr Ala Val Leu Val Gly Val Gly Val Ile Ala
    370                 375                 380

Gly Ile Tyr Tyr Leu Phe Thr His Ala Arg Thr Glu Arg Ala Lys His
385                 390                 395                 400

Gly Val Val Lys His Val Glu Thr Met Val Leu Ala Gln
                405                 410

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      xmpE del F sequence

<400> SEQUENCE: 3
gtcaaactct ttacgccgac g                                              21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      xmpE del R sequence

<400> SEQUENCE: 4
cgacaacacc aacagatact gc                                             22

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      xmpE 2copy F (xbaI) sequence

<400> SEQUENCE: 5
atgctctaga ctagatcttc tcgacgggca g                                   31

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      xmpE 2copy R (speI) sequence

<400> SEQUENCE: 6
atgatactag tccttgggga cttcgcgtgt cg                                  32

<210> SEQ ID NO 7
<211> LENGTH: 32
<212> TYPE: DNA
<213> ORGANISM: Artificial Sequence

```
<220> FEATURE:
<223> OTHER INFORMATION: Description of Artificial Sequence: Synthetic
      xmpE 2copy F (speI) sequence

<400> SEQUENCE: 7
atgatactag tctagatctt ctcgacgggc ag                                    32

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      xmpE 2copy CF sequence

<400> SEQUENCE: 8
ttcggctcag cattttccac                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      xmpE 2copy CR sequence

<400> SEQUENCE: 9
caatagtggt cgcgatgacg                                                  20

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      Pcj7 F sequence

<400> SEQUENCE: 10
gcagtaagga gaatcagaaa catcccagcg ctacta                                36

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      Pcj7 R sequence

<400> SEQUENCE: 11
acctcttcgg ttgtgtgcac gagtgtttcc tttcgttggg                            40

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      xmpE P 1 sequence

<400> SEQUENCE: 12
atgctctaga tccagtgtgg ttaagaagtc g                                     31

<210> SEQ ID NO 13
<211> LENGTH: 33
<212> TYPE: DNA
<213> ORGANISM: Artificial Sequence
<220> FEATURE:
```

```
<223> OTHER INFORMATION: Description of Artificial Sequence: Synthetic
      xmpE P 2 sequence

<400> SEQUENCE: 13
cgctgggatg tttctgattc tccttactgc agt                                   33

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      xmpE P 3 sequence

<400> SEQUENCE: 14
gtacccaacg aaaggaaaca ctcgtgcaca caaccgaaga ggt                         43

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      xmpE P 4 sequence

<400> SEQUENCE: 15
atgctctaga ttattgagcc agaaccatgg                                       30

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Pcj7/xmpE CF sequence

<400> SEQUENCE: 16
ctagatcttc tcgacgggca g                                                21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Pcj7/xmpE CR sequence

<400> SEQUENCE: 17
caatagtggt cgcgatgacg                                                  20

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      xmpE atg 1 sequence

<400> SEQUENCE: 18
atgctctaga tccagtgtgg ttaagaagtc g                                     31

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
```

-continued

```
       xmpE atg 2 sequence

<400> SEQUENCE: 19
gacctcttcg gttgtgtgca tgattctcct tactgcagtt a                          41

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      xmpE atg 3 sequence

<400> SEQUENCE: 20
taactgcagt aaggagaatc atgcacacaa ccgaagaggt c                          41

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      xmpE atg 4 sequence

<400> SEQUENCE: 21
atgctctaga ctcgctcttg tcgacaacac                                       30
```